(12) United States Patent
Artim Mann et al.

(10) Patent No.: US 9,994,863 B2
(45) Date of Patent: Jun. 12, 2018

(54) GLYPHOSATE TOLERANT CORN EVENT VCO-O1981-5 AND KIT AND METHOD FOR DETECTING THE SAME

(75) Inventors: Lori Artim Artim Mann, Hillsborough, NC (US); Vadim Beilinson, Cary, NC (US); Nadine Carozzi, Raleigh, NC (US); Rebekah Deter, Champaign, IL (US); Brian Vande Berg, Raleigh, NC (US); Alain Toppan, Cornebarrieu (FR); Laurent Beuf, Le Broc (FR); Georges Freyssinet, Saint-Cyr-au-Mont-d'Or (FR)

(73) Assignee: Genective, Chappes (FR)

( * ) Notice: Subject to any disclaimer, the term of this patent is extended or adjusted under 35 U.S.C. 154(b) by 746 days.

(21) Appl. No.: 14/235,219

(22) PCT Filed: Jul. 26, 2012

(86) PCT No.: PCT/EP2012/064712
§ 371 (c)(1),
(2), (4) Date: Jan. 27, 2014

(87) PCT Pub. No.: WO2013/014241
PCT Pub. Date: Jan. 31, 2013

(65) Prior Publication Data
US 2014/0325697 A1 Oct. 30, 2014

Related U.S. Application Data

(60) Provisional application No. 61/512,695, filed on Jul. 28, 2011.

(51) Int. Cl.
*A01H 5/10* (2018.01)
*C12N 15/82* (2006.01)
*C12N 9/10* (2006.01)
*C12Q 1/68* (2018.01)

(52) U.S. Cl.
CPC .......... *C12N 15/8275* (2013.01); *A01H 5/10* (2013.01); *C12N 9/1092* (2013.01); *C12Y 205/01019* (2013.01); *C12Q 1/6895* (2013.01); *Y10T 436/143333* (2015.01)

(58) Field of Classification Search
CPC ............. C12N 9/1092; C12N 15/8275; C12N 15/8274; C12Q 1/6895; A01H 5/10; C12Y 205/01019
See application file for complete search history.

(56) References Cited

U.S. PATENT DOCUMENTS

| | | | |
|---|---|---|---|
| 4,535,060 A | 8/1985 | Comai | |
| 5,436,389 A | 7/1995 | Pfund | |
| 5,591,616 A | 1/1997 | Hiei et al. | |
| 6,040,497 A | 3/2000 | Spencer et al. | |
| 6,294,711 B1 * | 9/2001 | Meulewaeter | C12N 15/8286 435/418 |
| 6,638,766 B2 * | 10/2003 | Albert | C07K 14/00 435/419 |
| 7,582,434 B2 * | 9/2009 | Behr | C12N 15/8275 435/6.12 |
| 7,834,249 B2 * | 11/2010 | Schouten | C12N 9/1092 435/252.3 |
| 2009/0137395 A1 * | 5/2009 | Chicoine | C12N 15/8275 504/206 |
| 2010/0071090 A1 * | 3/2010 | Hammer | C12N 15/8214 800/279 |

FOREIGN PATENT DOCUMENTS

| | | |
|---|---|---|
| EP | 0 507 698 A1 | 10/1992 |
| EP | 0 508 909 A1 | 10/1992 |
| EP | 1 167 531 A1 | 1/2002 |
| EP | 2 078 754 A2 | 7/2009 |
| WO | WO 92/04449 A1 | 3/1992 |
| WO | WO 92/06201 A1 | 4/1992 |
| WO | WO 95/06128 A2 | 3/1995 |
| WO | WO 97/04103 A2 | 2/1997 |
| WO | WO 2007/064828 A2 | 6/2007 |
| WO | WO 2008/100353 A2 | 8/2008 |
| WO | WO 2008/112019 A2 | 9/2008 |

OTHER PUBLICATIONS

Heck, G. R., et al. "Development and characterization of a CP4 EPSPS-based, glyphosate-tolerant corn event." Crop Science 45.1 (2005): 329-339.*
Padgette, Stephen R., et al. "Development, identification, and characterization of a glyphosate-tolerant soybean line." Crop science 35.5 (1995): 1451-1461.*
International Search Report (PCT/ISA/210) dated Dec. 3, 2012 (Three (3) pages).
Cheng, Z.M., et al., "Timentin as an alternative antibiotic for suppression of *Agrobacterium tumefaciens* in genetic transformation", Plant Cell Reports (1998) 17, pp. 646-649.
De La Riva, G. A., et al., "*Agrobacterium tumefaciens*: a natural tool for plant transformation", EJB Electronic Journal of Biotechnology ISSN: 0717-3458, vol. 1, No. 3, Dec. 15, 1998, pp. 118-133.
Dellaporta S.L., et al., "A plant DNA Minipreparation: Version II", Plant Molecular Biology Reporter, vol. 1, No. 4 (1983), pp. 19-21.
Depicker, A., et al., "Nopaline Synthase: Transcript Mapping and DNA Sequence", Journal of Molecular and Applied Genetics (1982), pp. 561-573.

(Continued)

*Primary Examiner* — Lee A Visone
*Assistant Examiner* — Weihua Fan
(74) *Attorney, Agent, or Firm* — Crowell & Moring LLP

(57) ABSTRACT

The present invention relates to the field of plant transformation with genes conferring tolerance to glyphosate. The invention particularly relates to a maize (corn) plant transformed with a gene encoding an EPSPS providing the plant tolerance to an application of glyphosate under conditions where this herbicide is effective in killing weeds.

The invention particularly concerns an elite transformation event VCO-Ø1981-5 comprising the gene construct and means, kits and methods for detecting the presence of the said elite event.

4 Claims, 5 Drawing Sheets

(56) References Cited

OTHER PUBLICATIONS

Guidance for risk assessment of food and feed from genetically modified plants, EFSA Journal (2011); 9(5):2150, pp. 1-37.

Fang, L., et al., "Sequence of two acetohydroxyacid synthase genes from *Zea mays*", Plant Molecular Biology 18 (1992), pp. 1185-1187.

Gardner, R., et al., "The complete nucleotide sequence of an infectious clone of cauliflower mosaic virus by M13mp7 shotgun sequencing", Nucleic Acids Research, vol. 9, No. 12 (1981), pp. 2871-2888.

Gelvin, S. B., "Gene exchange by design", Nature, vol. 433, Feb. 2005, pp. 583-584.

Kelley, P.M., et al., The Complete Amino Acid Sequence for the Anaerobically induced Aldolase from Maize Derived from cDNA Clones, Plant Physiol. (1986), vol. 82, pp. 1076-1080.

Komari, T., et al., "Vectors carrying two separate T-DNAs for co-transformation of higher plants mediated by *Agrobacterium tumefaciens* and segregation of transformants free from selection markers", The Plant Journal (1996) 10(1), pp. 165-174.

Lawrence C.J., et al., "Maize GDB, the community database for maize genetics and genomics", Nucleic Acids Research (2004), vol. 32, Database issue, pp. D393-D397.

Otten, L., et al., "Sequence and functional analysis of the left-hand part of the T-region from the nopaline-type Ti plasmid, pTiC58", Plant Molecular Biology (1991) 41, pp. 765-776.

Heck, G. R., et al, "Development and Characterization of a CP4 EPSPS-Based, Glyphosate-Tolerant Corn Event", Crop Science, vol. 45, No. 1, Jan. 2005, pp. 329-339, XP002687299.

\* cited by examiner

GLYPHOSATE TOLERANT CORN EVENT VCO-O1981-5 AND KIT AND METHOD FOR DETECTING THE SAME

The present invention relates to the field of plant transformation with genes conferring tolerance to glyphosate. The invention particularly relates to a maize (corn) plant transformed with a gene encoding an EPSPS providing the plant tolerance to an application of glyphosate under conditions where this herbicide is effective in killing weeds.

The invention particularly concerns an elite transformation event comprising the gene construct and means, kits and methods for detecting the presence of the said elite event.

BACKGROUND OF THE INVENTION

Glyphosate tolerant plants are known in the art and well studied in the past two decades. Glyphosate is an herbicide inhibiting EPSPS which is an enzyme whose activity is upstream of the aromatic amino acids pathway leading to the synthesis of the amino acids tyrosine, tryptophan and phenylalanine. Since glyphosate is a systemic total herbicide, tolerance in the plant when the herbicide is sprayed under usual agronomic conditions may only be achieved by genetic modification of all cells of the plants with an heterologous gene coding for a glyphosate insensitive EPSPS enzyme, either mutated or selected from microorganisms known to have evolved such insensitive EPSPS enzyme.

Glyphosate insensitive EPSPS, gene constructs and plants transformed with said gene constructs are disclosed inter alia in EP 507 698, EP 508 909, U.S. Pat. No. 4,535,060, U.S. Pat. No. 5,436,389, WO 92/04449, WO 92/06201, WO 95/06128, WO 97/04103, WO 2007/064828 and WO 2008/100353, and in references cited herein.

The biophysical characteristics of the EPSPS protein are essential to achieve a good level of tolerance to glyphosate. However, the choice of regulatory elements providing an adequate expression level of the insensitive protein in the plant is also important, as well as the selection of a transformation event, corresponding to a stable line with a stable and limited number of copies of the gene being inserted in the genome of the plant, as well as its stability in the locus where the gene has been inserted is also important to obtain glyphosate tolerance at a commercial level, sufficient for the plant to be used for the preparation of seeds to be planted in a field with a level of tolerance to glyphosate under agronomic conditions sufficient to allow use of the herbicide at effective concentrations to kill the weeds without affecting growing conditions and yields of the crop transformed with the gene encoding EPSPS protein.

Transformation events selected for the preparation of commercial varieties of glyphosate tolerant maize (corn) are known in the art, particularly disclosed in U.S. Pat. No. 6,040,497 and EP 1 167 531.

These varieties of the first generation used for the preparation of commercial plants currently used in the field have some drawbacks.

The event GA21 disclosed in U.S. Pat. No. 6,040,497 comprise multiple copies of a gene construct comprising a rice actin promoter and intron, a sequence coding for an optimized transit peptide, as disclosed in EP 505 909 and a sequence coding for a mutated plant EPSPS comprising two mutations as disclosed in WO 97/04103. The commercially required level of tolerance in the transformation event is obtained with a complex transit peptide and multiple copies of the chimeric gene construct.

The event NK603 disclosed in EP 1 167 531, is also a complex event with the combination of two gene constructs in one locus. The first gene construct comprises a rice actin promoter and intron, with a sequence coding for an *Arabidopsis* EPSPS transit peptide and a sequence coding for a type II EPSPS resistant to inhibition by glyphosate, isolated from *Agrobacterium* strain CP4. The second gene construct comprises the CaMV 35S promoter and the rice actin intron, with a sequence coding for an *Arabidopsis* EPSPS transit peptide and a sequence coding for a type II EPSPS resistant to inhibition by glyphosate, isolated from *Agrobacterium* strain CP4.

There is a need for a new generation of transformation events allowing a high glyphosate tolerance to maize (corn) plants grown under agronomic conditions with a single copy of the foreign gene construct in the plant genome.

SUMMARY OF THE INVENTION

The invention concerns a maize (corn) plant comprising the event VCO-Ø1981-5 representative seeds deposited with NCIMB with accession number 41842.

The invention also concerns a maize (corn) plant comprising the VCO-Ø1981-5 event characterized by the presence of a genomic flanking sequence-gene construct junctions comprising the sequences of SEQ ID NO: 1 and/or SEQ ID NO: 2 or SEQ ID NO: 3.

The invention also concerns corn plants progenies comprising the VCO-Ø1981-5 event of the invention, characterized by the presence of the said junctions sequences.

Probes to identify the presence of said junction sequences in a maize (corn) plant genome, as well as kits and methods for such identification comprising said probes and their uses, particularly a method for the detection of the VCO-Ø1981-5 event and primers, probes and a kit for such a detection are also part of the invention.

DETAILED DESCRIPTION OF THE INVENTION

"Transformation event" means a product of plant cell transformation with a heterologous DNA construct, the regeneration of a population of plants resulting from the insertion of the transgene into the genome of the plant, and selection of a particular plant characterized by insertion of the gene construct into a particular genome location.

"Gene construct" means, according to the invention, a gene constructed from different nucleotide sequences, comprising regulatory elements controlling the expression and translation of a coding sequence in a host organism. The host organism in the invention is particularly maize (corn), cells, tissues and whole plants. The gene construct comprises a promoter region, operably linked to a coding sequence and a terminator region. It may comprise enhancers, such as introns, generally linked downstream the promoter region and upstream the coding region. In the case of glyphosate tolerance, the coding sequence comprise a sequence coding for a chloroplast transit peptide, linked to the sequence coding for an EPSPS enzyme selected for its resistance to inhibition by glyphosate, either mutated or selected or selected and mutated from microorganism having developed resistance to glyphosate.

The gene construct in the event of the invention comprises a DNA molecule of a sugarcane ubiquitin promoter and intron, operably linked to a DNA molecule coding for the maize acetohydroxyacid synthase (AHAS) transit peptide, operably linked to a DNA molecule coding for the *Arthro-*

*bacter globiformis* EPSPS GRG23ACE5. The gene construct also comprises a terminator sequence, particularly the terminator sequence of the 35S CaMV transcript.

The various elements of the gene construct of the invention are isolated and operably linked according to usual techniques of molecular biology known and available to the person skilled in the art.

"Ubiquitin promoter and intron" means the promoter from sugarcane ubiquitin-4 gene and the intron from sugarcane ubiquitin-4 gene, from the non-coding 5' region of the ubiquitin-4 gene of *Saccharum officinarum* L. as disclosed in Albert and Wei (U.S. Pat. No. 6,638,766) and set forth in SEQ ID NO: 4 and 5, respectively.

"Maize AHAS chloroplast transit peptide" is the N-terminal transit peptide sequence derived from the *Zea mays* L. (maize) acetohydroxyacid synthase (AHAS) gene, as disclosed in Fang et al (1992) and set forth in SEQ ID NO: 6.

"*Arthrobacter globiformis* epspsgrg23ace5" means the nucleotide sequence as set forth in SEQ ID NO: 28 of WO 2008/100353. (SEQ ID NO: 7).

"35 CaMV terminator sequence" is the non-coding 3' end from the cauliflower mosaic virus which terminates mRNA transcription and induces polyadenylation as disclosed in Gardner et al (1981) and set forth in SEQ ID NO: 8.

"Plant transformation" and selection of transformed plants is widely disclosed in the art, and more particularly corn transformation. Techniques for corn transformation and breeding are now well known in the art, and particularly disclosed in laboratory notebooks and manuals such as "Transgenic Plants: Methods and Protocols (Methods in Molecular Biology)" (Leandro Peña, Humana Press Inc., 2005), "Heterosis and Hybrid Seed Production in Agronomic Crops" (Amarjit Basra, The Harwoth Press Inc., 1999) and "The Maize Handbook" (Michael Freeling and Virginia Walbot, Springer Lab Manuals, 1994). The transformation of corn is more particularly performed with an *Agrobacterium* mediated transformation comprising a transformation vector (Hiei and Komari, 1997, U.S. Pat. No. 5,591,616).

The transformation of a plant with a gene construct generally comprises the steps of
a) inoculating a plant cell with a strain of *Agrobacterium tumefaciens* comprising a transformation vector comprising the gene construct;
b) selecting the plant cells having integrated into their genome the gene construct of the invention;
c) regenerating a fertile plant from the selected plant cell;
d) pollinating the regenerated plant, and;
e) selecting progeny plants tolerant to high doses of glyphosate, then;
f) selecting the plants having stably integrated one unique copy of the gene construct of the invention.

"Transformation vectors" means a DNA molecule comprising the gene construct and additional DNA elements allowing introduction of the gene construct into a plant cell and integration of said gene construct into the genome of the plant cell. Transformation is an *Agrobacterium* mediated transformation, wherein the transformation vector comprises right and left borders of a T-DNA plasmid from *Agrobacterium tumefaciens* flanking the gene construct to be inserted. Such transformation vectors are well disclosed in the art and readily available to the person skilled in the art of plant molecular and cellular biology and plant transformation.

"Right and left borders of a T-DNA plasmid from *Agrobacterium tumefaciens*" are DNA sequences of the right and left border sequences from Ti plasmids and well known and disclosed in the art of plant transformation. More particularly, the right border (RB) sequence is used as the initiation point of T-DNA transfer from *Agrobacterium tumefaciens* to the plant genome, it is particularly the right border sequence of nopaline type T-DNA derived from plasmid pTiT37. (Depicker et al. 1982; Komari et al., 1996). The left border (LB) sequence defines the termination point of T-DNA transfer from *A. tumefaciens* to the plant genome, it is particularly the left border sequence from Ti plasmid pTiC58. (Komari et al., 1996; Otten et al., 1999).

"Transformed plants" mean plants having integrated into their genome the gene construct flanked with the full or a fragment of the sequence of the right and left borders of a T-DNA plasmid from *Agrobacterium tumefaciens*. All cells of the transformed plants have integrated into their genome the gene construct. The transformed plant is a fertile plant and more particularly a plant which agronomic properties (yield, grain quality, drought tolerance, etc.) are not impaired compared to the same plant not transformed.

"Insert DNA" is the gene construct flanked by RB and LB sequences and inserted in the plant genome at a specific locus.

The event is defined by a stable integration of the insert T-DNA of the invention at a specific locus in the maize (corn) genome.

The insertion defines two unique junctions DNA sequence wherein the insert T-DNA sequence joins the flanking maize genomic sequences. By reference to the insert T-DNA, there is a 5' junction DNA localized in the 5' part of the insert T-DNA and a 3' junction DNA localized in the 3' part of the insert T-DNA. Non limiting examples of the event VCO-Ø1981-5 junctions DNA (or so called "event VCO-Ø1981-5 DNA") are set forth in SEQ ID NO: 1, SEQ ID NO:2 or SEQ ID NO: 3.

The term "event" refers to the original transformed plant and progeny of the transformed plant that include the heterologous DNA. The term "event" also refers to progeny produced by a sexual outcross between the transformed plant and another variety in that the progeny includes the heterologous DNA.

The term «event» also refers to progeny produced by sexual backcrosses between a donor inbred line (the original transformed line and the progeny) comprising the insert DNA and the adjacent flanking genomic sequences and a recipient inbred line (or recurrent line) that does not contains the said insert DNA. After repeated back-crossing, the insert DNA is present in the recipient line at the same locus in the genome as in the donor line.

The term "event" or event sequence of VCO-Ø1981-5 also refers to the insert DNA from the original transformed plant comprising part or all of the insert DNA and adjacent flanking genomic sequences that would be transferred from the donor line to the recipient line.

The last backcross progeny would be selfed to produce progeny which are homozygous for the introgressed insert DNA.

These progeny would then be used as inbred parent line to produce hybrids.

A glyphosate tolerant maize (corn) VCO-Ø1981-5 (also named 6981 maize (corn)) can be bred by first sexually crossing a donor parental maize (corn) plant consisting of a maize (corn) plant grown from the transgenic maize (corn) plant VCO-Ø1981-5 (also named 6981 maize (corn)); representative seeds deposited with NCIMB with accession number 41842 and progeny thereof derived from transformation with the expression cassettes of the present invention that tolerates application of glyphosate herbicide, and a recipient parental maize (corn) plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the recipient parental (or recurrent) maize (corn) plant or a third parental maize (corn) plant, thereby producing a maize (corn) plant that tolerates the application of glyphosate herbicide.

Methods for producing a hybrid maize (corn) seed are well known in the art. The method comprises crossing the plant comprising the VCO-Ø1981-5 event deposited on 13 May 2011 by GEMSTAR, rue Limagrain, BP-1, 63720 Chappes, FRANCE, with NCIMB with accession number 41842 or said plant progeny comprising the VCO-Ø1981-5 event with a different maize (corn) plant and harvesting the resultant hybrid maize (corn) seed comprising the VCO-Ø1981-5 event.

It is also to be understood that two different transgenic plants can also be mated to produce offspring that contain two or more independently segregating added, transgenes. A method for producing a maize (corn) plant that contains in its genetic material two or more transgenes, wherein the method comprises crossing the maize (corn) plant comprising the VCO-Ø1981-5 event deposited with NCIMB with accession number 41842 or said plant progeny comprising the VCO-Ø1981-5 event with a second plant of maize (corn) which contains at least one transgene so that the genetic material of the progeny that results from the cross contains the transgene(s) operably linked to a regulatory element and wherein the transgene is selected from the group consisting of male sterility, male fertility, insect resistance, disease resistance and water stress tolerance and herbicide resistance (wherein the transgene confers resistance to an herbicide selected from the group consisting of imidazolinone, sulfonylurea, glyphosate, glufosinate).

Selfing of appropriate progeny can produce plants that are homozygous for both added, exogenous genes. Said maize (corn) plant comprising two or more transgenes would be used to produce hybrid maize (corn) seeds wherein the method comprises crossing the said maize (corn) plant with a different maize (corn) plant and harvesting the resultant hybrid maize (corn) seeds comprising two or more transgenes.

Back-crossing to a parental plant and out-crossing with a non-transgenic plant are also contemplated. Descriptions of other breeding methods that are commonly used for different traits and crops can be found in one of several references, e.g., A. Hallauer and J. B. Miranda in Quantitative genetics in maize breeding. (2nd edition, Iowa State University press) and R. Bernardo in Breeding for quantitative traits in plants. (Stemma press.com).

The term «event» also refers to a maize (corn) plant produced by vegetative reproduction from the maize (corn) plant comprising the VCO-Ø1981-5 event deposited with NCIMB with accession number 41842 or said plant progeny comprising the VCO-Ø1981-5 event. Vegetative reproduction can be initiated from a plant part as for example cells, tissues such as leaves, pollen, embryos, roots, root tips, anthers, silks, flowers, kernels, ears, cobs, husks, stalks or tissue culture initiated from said plant part. The term event also refers to said plant part.

The term event concerns a glyphosate tolerant corn, comprising in its genome the nucleotide sequences that are at least 95%, preferably at least 96, 97, 98, or 99% identical to SEQ ID NO: 1 or SEQ ID NO: 2 or SEQ ID NO: 3.

The invention also concerns the polynucleotide sequences comprising SEQ ID NO: 1 or SEQ ID NO: 2 or SEQ ID NO: 3 and having any length from 25 nucleotides to 5092 nucleotides.

Particularly the invention concerns the polynucleotide sequences of SEQ ID NO: 1, SEQ ID NO: 2 and SEQ ID NO: 3 specific to event VCO-Ø1981-5. These polynucleotide sequences are suitable for selectively identifying the event VCO-Ø1981-5 in different biological samples. By biological samples, it is to be understood a plant, plant part or plant material such as cells, tissues as leaves, pollen, embryos, roots, root tips, anthers, silks, flowers, kernels, ears, cobs, husks, stalks or seeds. It is also to be understood a processed products comprising or derived from plant part or plant material.

Methods for the detection of the presence or absence of specific DNA elements in a plant genome are well known in the art. Main techniques comprise DNA sequence amplification, particularly with Polymerase Chain Reaction, with specific primers allowing amplification of the DNA sequence, and hybridization with a probe specific for the DNA sequence.

The invention comprises a method for the identification of the presence or the absence of the transformation event VCO-Ø1981-5 of the invention, particularly with one of the known techniques.

In a particular embodiment of the invention, the method comprises the steps of:
 a) extracting DNA from a biological sample obtained from a maize (corn) plant, tissue or cell;
 b) contacting said extracted DNA with a first and second primers of appropriate length selected to allow production of an amplicon DNA molecule comprising all or part of the event sequence of VCO-Ø1981-5;
 c) performing an amplification reaction to produce amplicon DNA molecules, and;
 d) detecting the presence or the absence of a nucleotide sequence comprising all or part of the event sequence of VCO-Ø1981-5 in the amplicon molecule.

Primers have generally a length comprised between 10 and 30 nucleotides, and are selected and prepared according to techniques well known to the person skilled in the art of molecular biology.

In a particular embodiment of the invention, the amplicon molecule comprising all or part of the event sequence of VCO-Ø1981-5 comprises the event junction sequence set forth in SEQ ID NO: 1 and/or the event junction sequence set forth in SEQ ID NO: 2 and/or a sequence that is at least 95%, preferably at least 96, 97, 98, or 99% identical to SEQ ID NO: 1 or SEQ ID NO: 2.

Advantageously, the first and second primers comprises sequences homologous to a sequence fragment of the event sequence set forth in SEQ ID NO: 3, and are selected to be flanking the event VCO-Ø1981-5 sequence and to generate an amplicon comprising the DNA sequences set forth in SEQ ID NO: 1 and SEQ ID NO: 2.

Preferred primers comprise the DNA sequences set forth in SEQ ID NO: 11 and SEQ ID NO: 12.

In another embodiment of the invention, the method comprises the steps of:
 a) extracting DNA from a biological sample obtained from a maize (corn) plant, tissue or cell;

b) contacting said extracted DNA with probe(s) of sufficient length to hybridize under stringent conditions with a nucleotide sequence that specifically detect at least one of VCO-Ø1981-5 junction sequence;
c) subjecting the extracted DNA and probe(s) to stringent hybridization conditions, and;
d) detecting the hybridization of the probe(s) to the extracted DNA, wherein detection indicates the presence of an event VCO-Ø1981-5 sequence.

The invention also concerns a method for producing a glyphosate tolerant plant comprising breeding a plant of the invention, comprising the event VCO-Ø1981-5 sequence, and selecting progenies by detecting the presence of the event VCO-Ø1981-5 sequence, particularly with the detection method of the invention.

"Amplicon" refers to the product obtained by amplification with a specific pair of primers of a target nucleotide sequence comprised in a nucleotide template sequence.

Primers, probes and methods for the identification of the presence or absence of a specific DNA or amplicon sequence in a corn genome are well known in the art, particularly disclosed in paragraphs [0027] to [0043] of EP 1 167 531 which are incorporated herein by reference, as well as publications cited herein.

Stringent conditions are defined as following. For sequences comprising more than 30 bases, Tm is defined by the equation: Tm=81.5+0.41 (% G+C)+16.6 Log (concentration in cations)–0.63 (% formamide)–(600/number of bases) (Sambrook et al., 1989).

For sequences shorter than 30 bases, Tm is defined by the equation: Tm=4(G+C)+2(A+T).

Under appropriate stringency conditions, in which non-specific (aspecific) sequences do not hybridize, the temperature of hybridization is approximately between 5 and 30° C., preferably between 5 and 10° C. below Tm and hybridization buffers used are preferably solutions of higher ionic force like a solution 6*SSC for example.

The invention also concerns a kit for detecting the presence or absence of the VCO-Ø1981-5 event of the invention in a biological sample, wherein it comprises primers and/or probes amplifying or hybridizing to a polynucleotide sequence comprising an event VCO-Ø1981-5 DNA sequence.

The invention particularly comprises a first primer of 10 to 30 nucleotides, comprising a sequence homologous to a sequence fragment of SEQ ID NO: 3 and a second primer of 10 to 30 nucleotides comprising a sequence having complementarity to a sequence fragment of SEQ ID NO: 3, the first and the second primers flanking an event VCO-Ø1981-5 DNA sequence and generating an amplicon molecule comprising SEQ ID NO: 1 or SEQ ID NO: 2.

Particularly, said first and second primers comprise the sequences set forth in SEQ ID NO: 11 and SEQ ID NO: 12, respectively.

The invention also concerns an isolated nucleotide sequence comprising, or consisting essentially of, a sequence set forth in SEQ ID NO: 11 and/or SEQ ID NO: 12.

The invention also concerns an isolated nucleotide sequence comprising a sequence set forth in SEQ ID NO: 1 and/or SEQ ID NO: 2, particularly comprising, or consisting essentially of, the sequence set forth in SEQ ID NO: 3 or a fragment thereof and/or a sequence that is at least 95%, preferably at least 96, 97, 98, or 99% identical to SEQ ID NO: 1 or SEQ ID NO: 2 or SEQ ID NO: 3.

Techniques for gene constructions as well as techniques for gene identification using amplification techniques such as PCR or hybridization techniques are well known in the art, and particularly disclosed in laboratory notebooks and manuals such as Sambrook & Russel (2001, Molecular Cloning: A Laboratory Manual, Cold Spring Harbor, N.Y.).

FIGURES

Figure 3:
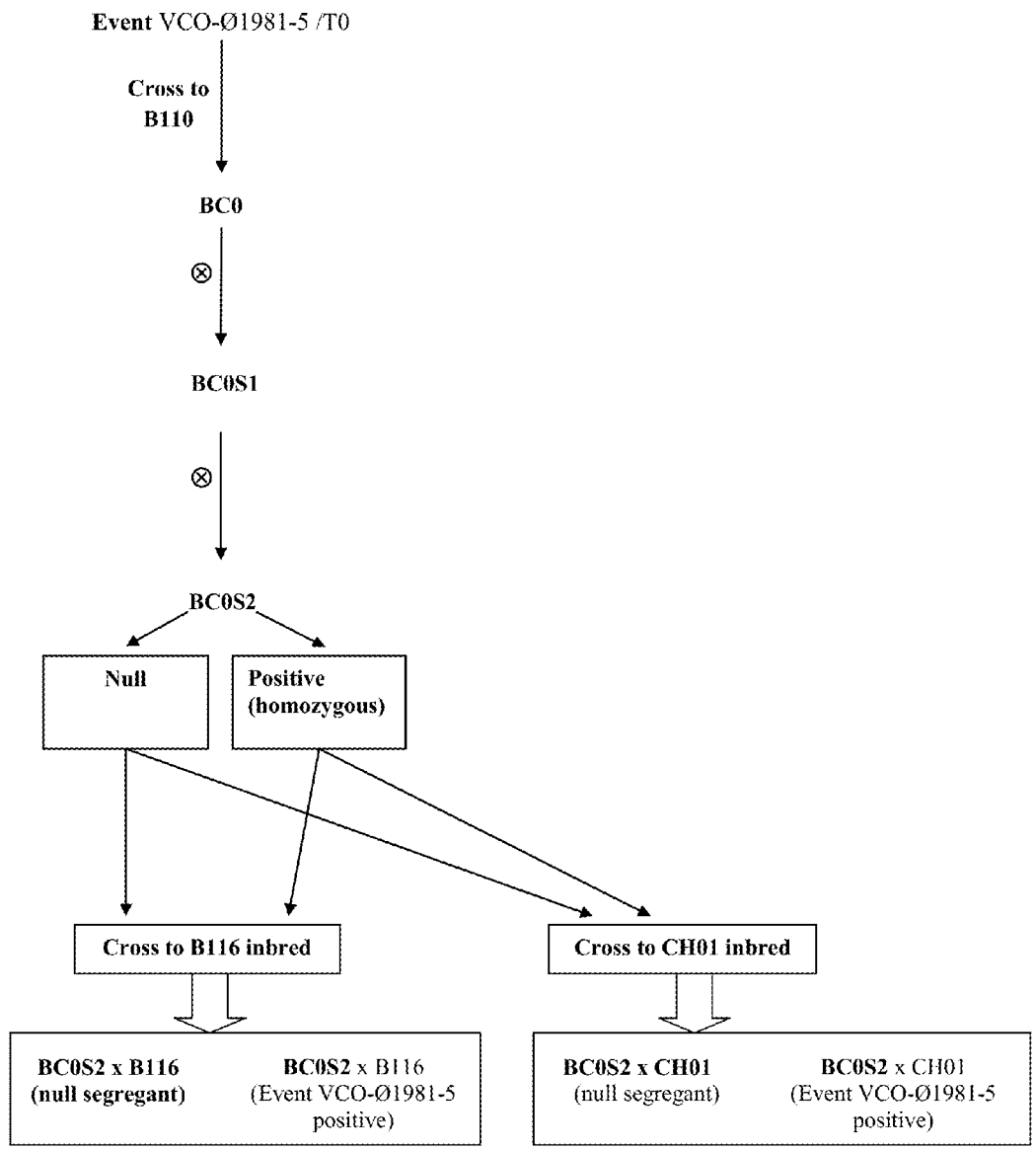

FIG. 3 describes the breeding diagram for event VCO-Ø1981-5.

Figure 4:
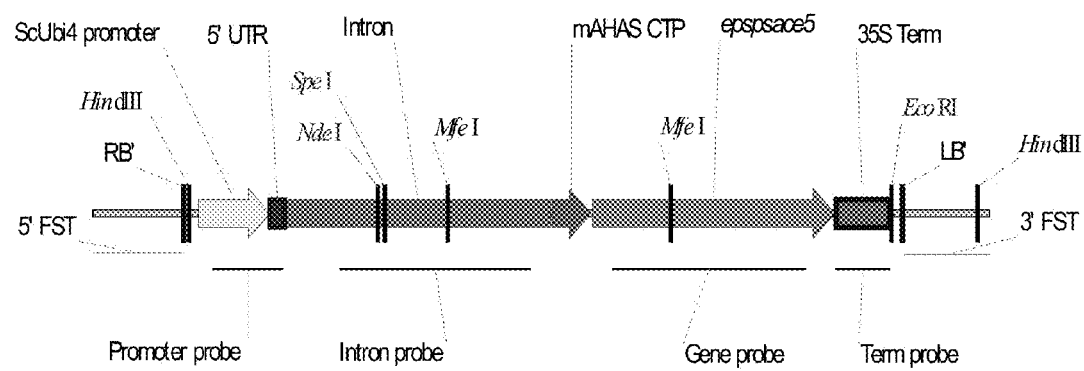

FIG. 4 represents the EPSPS GRG23ACE5 expression cassette within the T-DNA region.

Figure 5:
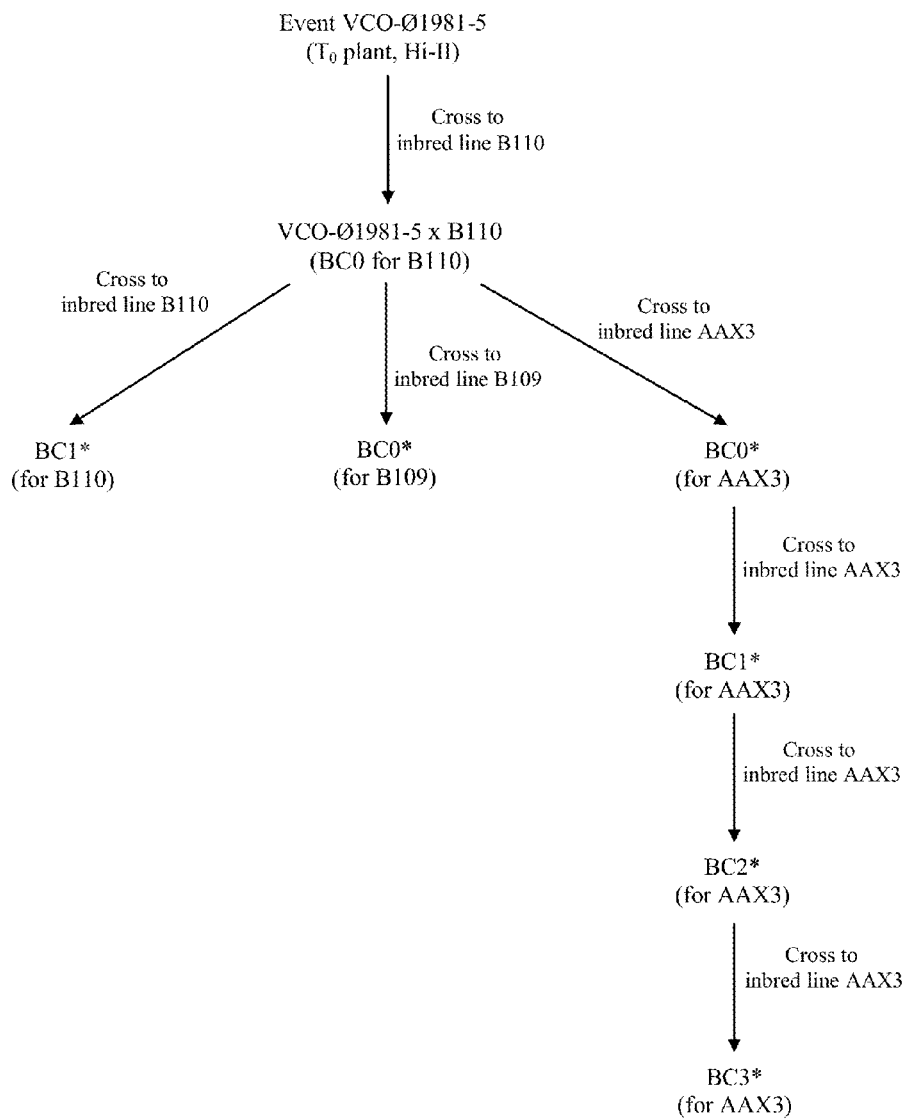

FIG. 5 represents a segregation analysis carried out in the following generation for the B110 and B109 crosses, and in the next 4 generations for line AAX3.

EXAMPLES

Abbreviations, Acronyms, and Definitions

| | |
|---|---|
| AHAS | Acetohydroxyacid synthase |
| BLAST | Basic Local Alignment Search Tool |
| Bp | Base pair |
| CaMV | Cauliflower mosaic virus |
| CHI-test | Pearson's chi-square test |
| CTP | Chloroplast transit peptide |
| DNA | Deoxyribonucleic acid |
| EPSPS | 5-enolpyruvylshikimate-3-phosphate synthase (protein) |
| epsps | 5-enolpyruvylshikimate-3-phosphate synthase (DNA sequence) |
| FST | Flanking sequence tag |
| GRG23ACE5 | Modified EPSPS from *Arthrobacter globiformis* |
| kbp | kilobase pairs |
| LB | Left border |
| PCR | Polymerase chain reaction |
| RB | Right border |
| T-DNA | Transferred-DNA |
| Ti | Tumor-inducing |
| Vir | Virulence genes of *Agrobacterium* |

I. Production of Glyphosate Tolerant Event VCO-Ø1981-5

Maize event VCO-Ø1981-5 was generated using a standard *Agrobacterium* mediated transformation protocol (Hiei and Komari, 1997). *Agrobacterium* contains a tumour-inducing (Ti) plasmid, which includes virulence (vir) genes and a transferred-DNA (T-DNA) region. Genes of interest can be inserted into the T-DNA region and thereafter transferred to the plant nuclear genome. The use of a Ti plasmid with the tumor-inducing genes deleted is commonly known as disarmed *Agrobacterium*-mediated plant transformation. Wounded plant cells produce phenolic defense compounds, which trigger the expression of the *Agrobacterium* vir genes. The encoded virulence (Vir) proteins process the T-DNA region from the Ti-plasmid, producing a 'T-strand'. After the bacterium attaches to a plant cell, the T-strand and several types of Vir proteins are transferred to the plant through a transport channel. Inside the plant cell, the Vir proteins interact with the T-strand, forming a T-complex. This complex targets the nucleus, allowing the T-DNA to integrate into the plant genome and express the encoded genes (Gelvin, 2005).

The recipient organism is the dent type of *Zea mays*, which belongs to the genus *Zea* of the family Gramineae (Hi-II stock material). This material is supplied in the form of two separate lines Hi-IIA and Hi-IIB. These lines are then crossed and the resulting embryos are used as target tissue for transformation. Hi-IIA and Hi-IIB are partially inbred lines selected out of a cross between corn inbred lines A188 and B73. As the recipient organism, hybrid Hi-II of *Zea mays* was produced by crossing the partially inbred Hi-IIA and Hi-IIB lines which were obtained from Maize Genetics COOP Stock Center (Urbana, Ill., USA). The T-DNA region in transformation vector pAG3541 was introduced using *Agrobacterium* into the hybrid Hi-II by co-cultivation (approximately 72 hours at 22° C. in the dark) with immature maize embryos. Transformed callus was selected on glyphosate-containing medium as a selective agent. The antibiotic timentin (200 ppm) was included in tissue culture media to eliminate *Agrobacterium* cells from the callus after transformation (Cheng et al., 1998).

Figure 1:
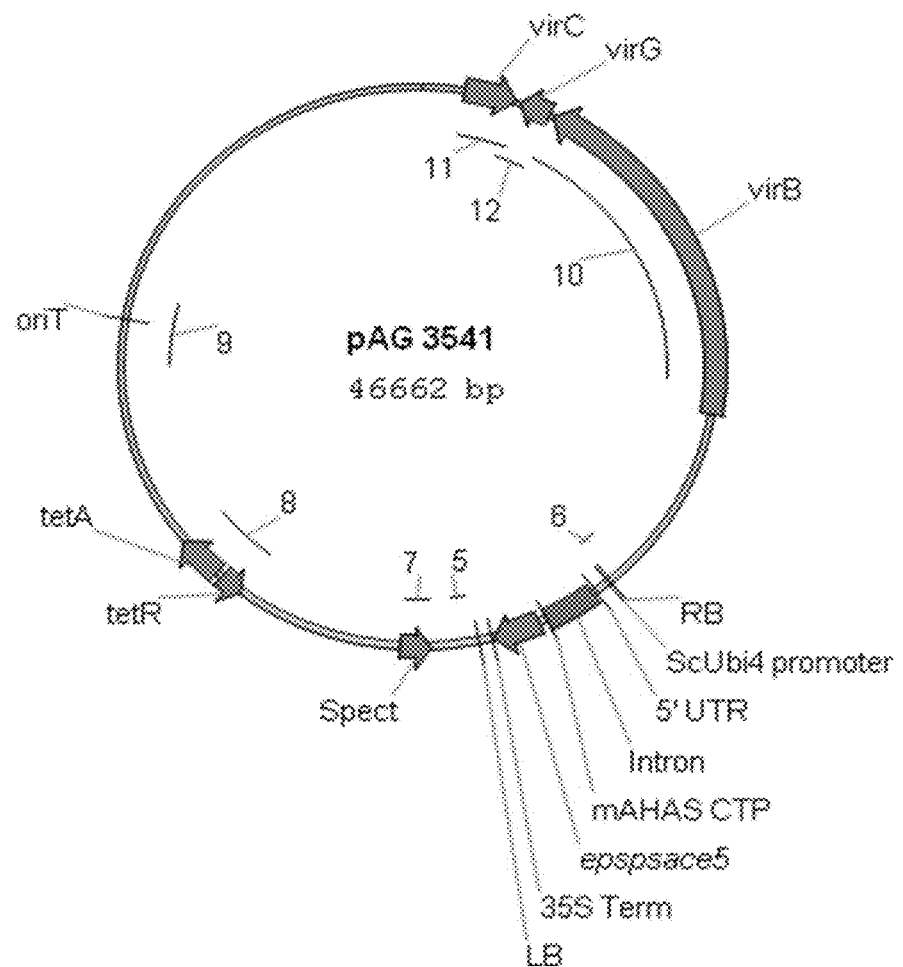
FIG. 1 represents the transformation vector pAG3541.

The transformation vector pAG3541 (FIG. 1) was used to transfer the epsps grg23ace5 expression cassette to maize. Only the T-DNA existing between the right and left border (RB and LB) sequences respectively is integrated into the maize genome. The DNA regions outside the T-DNA borders are not transferred. Outside these borders bacterial antibiotic resistant marker genes are required for the introduction and maintaining of the vector in the *Agrobacterium* cells. The vir genes are required for the production of the T-DNA transfer complex (De la Riva et al., 1998).

Out of 100 events generated in T0, VCO-Ø1981-5 event was selected through multiple evaluation field trials for glyphosate tolerance and agronomic performances like germination, vegetative characteristics (such as plant height, grain weight) and reproductive characteristics (such as days to 50% pollen shed, days to 50% silking, yield).

Figure 2:
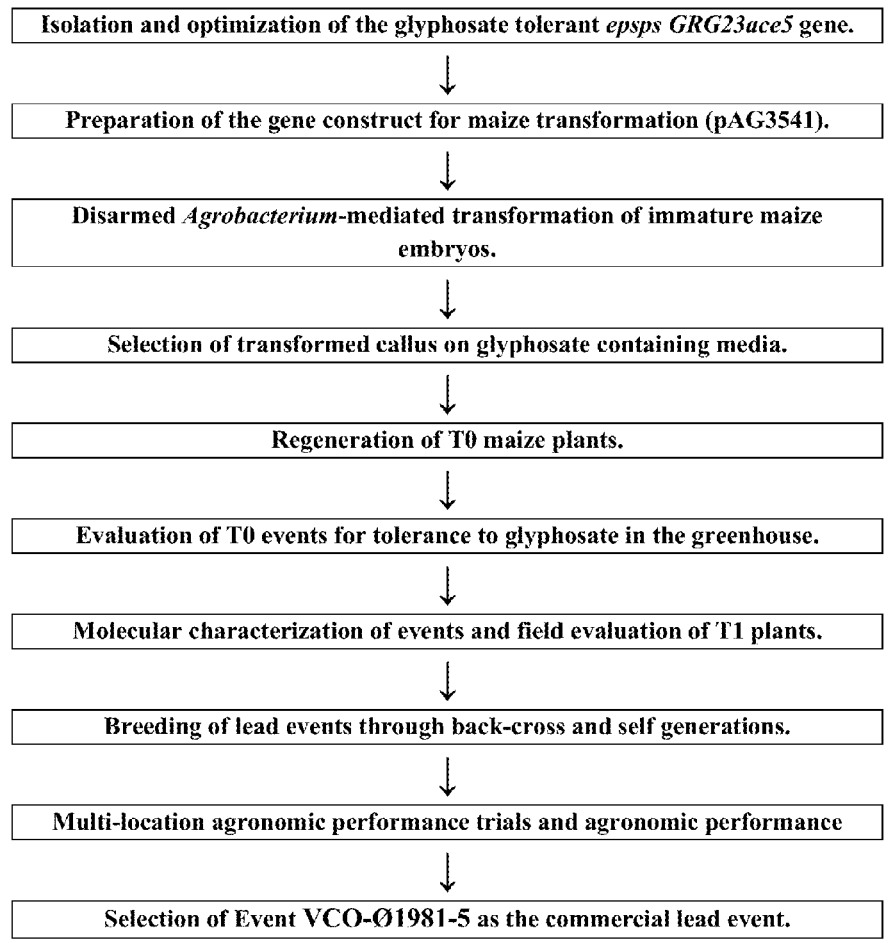
FIG. 2 represents the schematic diagram of the selection of event VCO-Ø1981-5.

The schematic diagram of the selection of event VCO-Ø1981-5 is provided on FIG. 2.

Event VCO-Ø1981-5 was also selected for good molecular characteristics based on the unicity and integrity of the insert and the stability of the genomic insertion locus and its inheritance.

More specifically, event VCO-Ø1981-5 was selected for its low level of allergenicity risk. Twelve Open Reading Frames (ORFs), created by the insertion of the T-DNA in the genome, have been identified at the junctions between the T-DNA and the maize genome. For this analysis, we consider that ORFs are any potential coding region between two stop codons as defined by the European Food safety Authority (EFSA). Bioanalysis of ORFs was first performed, followed by analysis for putative allergenic motifs in the determined ORFs using an 80 amino acids (AA) sliding window and 8 AA exact match. Analysis was performed according to Codex Alimentarius (2003) and using AllergenOnline Database Version 11 from February 2011 (http://www.allergenonline.org/databasefasta.shtml). Two potential hits were identified using the 80 AA sliding window, but it is highly unlikely that the identified genetic sequence would generate a translatable mRNA sequence and since these sequences were identified from the native maize genome, there is no impact to the allergenicity risk assessment. Finally, event VCO-Ø1981-5 was selected due to its advantageous location in a genomic region harboring a good recombination rate. This characteristic is notably important for the conversion program in which the event will be further used.

FIG. 3 describes the breeding diagram for event VCO-Ø1981-5.

II. Donor Genes and Regulatory Sequences

A. Transformation Vector Map

Event VCO-Ø1981-5 was produced by disarmed *Agrobacterium*-mediated transformation using the plasmid pAG3541. This transformation vector contains the epsps grg23ace5 expression cassette within the T-DNA region (FIG. 4).

B. Description of the Genes and Regulatory Sequences

A synthetic coding region sequence comprising a maize chloroplast transit peptide (acetohydroxyacid synthase) (Fang et al., 1992) and a gene encoding EPSPS GRG23ACE5 enzyme was generated. The synthetic gene was subcloned downstream from the ubiquitin-4 promoter from *Saccharum officinarum* L. (Albert and Wei, 2003) and upstream from the terminator 35S of Cauliflower mosaic virus (Gardner et. al., 1981) to create plasmid pAX3541. The promoter:gene::terminator fragment from this intermediate plasmid (based on pSB11, Japan Tobacco, Inc. (Hiei and Komari, 1997)) was mobilized into *Agrobacterium tumefaciens* strain LBA4404, which also harbors the plasmid pSB1, using triparental mating and plating on media containing spectinomycin, streptomycin, tetracycline and rifampicin to form a final plasmid, pAG3541. Rifampicin is included as an additional selection for *Agrobacterium* as the rifampicin resistance marker gene is present in the *Agrobacterium* chromosomal DNA. The integrity of cointegrate product of pSB1 and pAX3541-plasmid pAG3541 was verified by Southern hybridization.

The amino acid sequence of the wild-type EPSPS isolated from *Arthrobacter globiformis* was altered using a directed evolution technique resulting in the EPSPS GRG23ACE5 protein described herein and expressed in event VCO-Ø1981-5. The deduced amino acid sequence of the EPSPS GRG23ACE5 protein is shown below (SEQ ID NO: 23).

```
metdrlvipg sksitnrall laaaakgtsv lvrplvsadt safktaiqal ganvsadgdd wvveglgqap nldadiwced agtvarflpp fvaagqgkft vdgseqlrrr plrpvvdgir hlgarvsseq lpltieasgl aggeyeieah qssqfasgli maapyarqgl rvkipnpvsq pyltmtlrmm rdfgietstd gatvsvppgr ytarryeiep dastasyfaa asavsgrrfe fqglgtdsiq gdtsffnvlg rlgaevhwas nsvtirgper ltgdievdmg eisdtfmtla aiapladgpi titnigharl kesdrisame snlrtlgvqt dvghdwmriy pstphggrvn chrdhriama fsilglrvdg itlddpqcvg ktfpgffdyl grlfpekalt lpg
```

III. Transgene Copy Number Analysis

Maize genomic DNA was isolated (Dellaporta et al., 1983) and quantified by fluorimetry. DNA restriction, gel electrophoresis, Southern blotting and hybridization with radiolabeled probes were carried out according to standard procedures (Sambrook et al., 1989). Total genomic DNA was purified from event VCO-Ø1981-5 and digested with appropriate restriction endonucleases to determine both insert copy number and insert integrity.

Templates for radioactive probes synthesis were prepared using standard PCR methods. Oligonucleotide primers specific to promoter and terminator sequences in the T-DNA were used to generate a DNA probe specific for the T-DNA insert. The DNA probe was labeled with $^{32}$P α-dCTP using Ready-To-Go DNA labeling beads (GE Health). The labeled probe was purified over Micro Bio-Spin P-30 Tris-Chromatography Columns (BioRad). Hybridizations were carried out at 65° C. (Church, 1984). After hybridization, blots were washed at 65° C., with the final wash containing 1% (w/v) sodium dodecyl sulfate at pH 7.0. Blots were exposed to Kodak AR X-OMAT film using a Kodak intensifying screen at −80° C.

Genomic DNA from event VCO-Ø1981-5 corn, BC1 negative segregant corn, and B110 inbred corn was digested with the restriction enzymes HindIII and NdeI (New England Biolabs, Ipswich, Mass.) independently. Each of these restriction enzymes cuts once within the T-DNA region. When hybridized with the epsps grg23ace5 gene probe, the resulting number of hybridization products would indicate the insert copy number within the maize genome. Both digests produced a single band indicating a single copy of the insert present.

Genomic DNA from event VCO-Ø1981-5 corn, BC1 negative segregant corn, and B110 inbred corn was digested with a combination of HindIII and EcoRI, and independently with MfeI (New England Biolabs, Ipswich, Mass.). A set of four independent probes (ScUbi4 promoter, ScUbi4 intron, epsps grg23ace5 gene, and 35S terminator) were used to confirm the integrity of the expression cassette structure The results of the analysis indicated that the epsps grg23ace5 expression cassette was intact and the functional components were found and verified in the expected order in the inserted DNA.

Southern blot analysis was conducted to verify the absence of the transformation plasmid components outside of the transferred T-DNA region. Maize genomic DNA (VCO-Ø1981-5 event and appropriate negative controls) was digested with a combination of HindIII and EcoRI, and independently with MfeI (New England Biolabs, Ipswich, Mass.). The *Agrobacterium* plasmid pAG3541 was included as a positive control for hybridization of the transformation plasmid components. The probes used were designed to hybridize to the functional components of the plasmid including the sequence of aad, tetR, tetA, oriT, virC, virG, and virB.

Southern blot analysis results indicate that none of the vector probes hybridized to VCO-Ø1981-5 genomic DNA confirming the absence of the sequences of the functional components of the plasmid in event VCO-Ø1981-5. These same probes however did show hybridization with the plasmid vector control on each blot indicating that if the vector sequences were inadvertently transferred to event VCO-Ø1981-5 corn, they would have been detected in this analysis.

Southern blot analysis was conducted on multiple generations of event VCO-Ø1981-5 progeny to evaluate the stability of the T-DNA sequence insertion. Genomic DNA isolated from leaf material of VCO-Ø1981-5 plants from four successive breeding generations (BC0, BC1, BC3, and BC4) and negative controls were digested with the restriction enzyme HindIII (New England Biolabs, Ipswich, Mass.) which, as noted earlier, cuts once within the T-DNA region. When hybridized with the probe specific for the epsps grg23ace5 gene, VCO-Ø1981-5 produces a single band approximately 4.0 kb in size. The transformation plasmid pAG3541 was included as a hybridization control. All four generations analyzed showed an identical hybridization pattern producing the identical 4.0 kb band. If the genetic insert were unstable within the maize genome through successive breeding of the event, one would expect to detect changes in the banding pattern produced. The data indicates a stable insertion site in event VCO-Ø1981-5.

IV. Sequencing of the Insert and Flanking Genomic DNA

Southern blot analysis has demonstrated that event VCO-Ø1981-5 contains a single intact T-DNA insert containing a single expression cassette. The sequence of the transgenic locus including 5' and 3' FSTs (flanking sequence tags) and the sequence of the pre-insertion locus (locus in the corn genome where the transgene was inserted) have been determined.

The maize genomic sequences flanking the T-DNA insertion in event VCO-Ø1981-5 were obtained by Genome Walker™ (Clontech) (5'FST) and direct PCR (3'FST). Using the DNA sequences generated, a BLAST search (Altschul et al., 1997) was performed against the Maize Genetics and Genomics Database (Lawrence et al., 2004). Both the 5' and 3' FST sequences mapped to chromosome 1.

700 bp were obtained for the 5' FST and 700 bp for the 3' FST. The enzyme SspI was used for generating the library. The T-DNA specific primers used are listed in the following Table 1.

TABLE 1

| | Primer | 5'-->3' sequence | SEQ ID |
|---|---|---|---|
| 3'FST | Ace5-1 | ACAGGATCGCTATGGCGTTTTCAATCC | 17 |
| | Ace5-2 | ATGCGTCGGGAAGACCTTTCCTGGCTTC | 18 |
| | O39 | CACCAGGGAGGAGGCAACAACAAGTAG | 19 |
| 5'FST | Scubi-NewR | AGAAAGAGTCCCGTGAGGCTACGGCAC | 20 |
| | Scubi2-Rev | CTGGGATTTGGATGGATGAGGCAAGGAG | 21 |
| | Scubi1-Rev | AGAGGTCGCCGCGGAGATATCGAGGAG | 22 |

The insertion site could be mapped using a BLAST search against the Maize Genetics and Genomics Database (http://www.maizegdb.org/). It is located in the chromosome 1, more precisely on the BAC: AC185611.

To confirm the FST result, primers were deduced from the sequence obtained by the Genome Walker strategy and used to directly amplify the 5' and 3' FST sequence from Hi-II and VCO-Ø1981-5 (6981). The expected PCR products were obtained and sequenced. The sequences obtained were found identical as the one obtained from the Genome Walker which is thus considered as accurate.

The Map of inserted T-DNA, gene construct of the invention flanked with the right and left border and the flanking sequences (SEQ ID NO: 9 and SEQ ID NO: 10) is described on FIG. 4.

The 3' flanking sequence (SEQ ID NO: 9) has the following sequence:

gttctcagagggagatgggcggcaagggcggcgggggtggtggcaagggc ggcggcgggggtggtggcaagggcggaggaggttttggtggcaagagcgg cggcgggggtggtggcaagggcggaggaggtgttggtggcaagagcggcg gcggcaagtcaggcggcggcggcggtgggggctatggtggtggagggaag tcaggctccggcggcagtggcggcgacggaatgatgaaggcgcccggcgg cagtggcgagtacatctcccgctctgtcttcgaggccagcccgcaggtgt tcttccatggcctccaccagggaggaggcaacaacaagtagatccatcta gctagactgctgctgctacttcacaagcttgggacgatgtgtgatcatgc atgcttggactggcatcagtctctatgtagcttctgaataaaataaaatg taacgatgctcgattgtgtttcacttgctcgcttgtttcagccaagttat tatatatcatcaggctcgtacgtcagctatatatatatatatatatat atatatatatatatatatatatatatatatatatatatatatatat atatatatatatatacacacacacacatatgcaggtgcatggattgtgca acgcgaatgtgtgattgtgctaatccgttagttgatgccgtttgttgctt The 5' flanking sequence (SEQ ID NO: 10) has the following sequence:

tttcctcattttcttttcccgcttttgtttcaattttcttgggtaatg tacagtgagtatatttttcttgttcttttctcatggccaaaatccaca atggatcgatgaattagctgtcgttgttgccaacaacaacaacagaacaa -continued

```
aatcacgtgacgtactagcacaatgcaagtagccaaactgagcttccggg caccgacgaacggttgcacgccatcggcgggaaggaacaggccgggctgt caatggacaaacgggccgccaagctggagggagtgtcatgggctttgaga accatcgtcagggtccagtttattcttttgttttattaaaggcggtaaa ctcggggaacgaatatactaggaaaaacactagccagtcagagtcagtca aagtggactgagttaaaattgcaacgacacacacgcagcagtcagggcgt cgggaatgaacaatggatgaatttattataatctgaagaaaacgaaggga cacagccactacgaacactggggagtggggagtgaatgaatgaatgcatt ccactggaccgttccagcgcttcgtgtgcctcgctagatgcgctgaacac tcgaacgccatggacctcgctccgctctctatatatagagggaaggcctt cagtctactcctcgggatataccactgaacgtcaccaagaagatcagtac
```

Additionally, the entire T-DNA insert in event VCO-Ø1981-5 was sequenced and verified to be identical to that in transformation vector pAG3541. During the transformation integration process, the right and left border sequences do not typically remain intact and minor deletions in both were identified in event VCO-Ø1981-5.

A complete sequence comprising the entire T-DNA insert sequence and the flanking genomic sequence is listed as SEQ ID NO: 3.

V. Inheritance of the Glyphosate Tolerant Trait

During performance evaluation of event VCO-Ø1981-5, the locus containing epsps grg23ace5 was crossed with 3 inbred lines (B110, B109, AAX3). Progeny plants for each line were then sprayed with glyphosate to identify plants that inherited and expressed epsps grg23ace5 and assess the segregation ratio into each of the lines. The progenitor line for testing was generated by pollinating line B110 with the parental T0 plant for event VCO-Ø1981-5, which yielded a BC0 line (B110×VCO-Ø1981-5). These BC0 seeds were germinated and plants were crossed simultaneously with lines B110, B109 and AAX3. Segregation analysis was carried out in the following generation for the B110 and B109 crosses, and in the next 4 generations for line AAX3 (FIG. 5).

All glyphosate sprays were carried out at either 1×, 4×, or 8× the spray rate in outdoor field plots (1× was 540 g of glyphosate, acid form/ha). Positive segregants that survived the spray were scored as "tolerant", while negative segregants did not survive the spray and were scored as "sensitive".

TABLE 2

| Generation (line) | No | Gly. S.R. | Obs. Tol. | Obs. Sens. | Exp. Tol. | Exp. Sens. | % Tol. | CHI test value |
|---|---|---|---|---|---|---|---|---|
| BC1 (B110) | 9 | 4x | 7 | 2 | 4.5 | 4.5 | 77.8% | 0.096 |
| BC1 (B110) | 7 | 8x | 2 | 5 | 3.5 | 3.5 | 28.6% | 0.257 |
| BC0 (B109) | 10 | 4x | 5 | 5 | 5 | 5 | 50.0% | 1.000 |
| BC0 (B109) | 11 | 8x | 5 | 6 | 5.5 | 5.5 | 45.5% | 0.763 |
| BC0 (AAX3) | 28 | 1x | 12 | 16 | 14 | 14 | 42.9% | 0.450 |
| BC1 (AAX3) | 227 | 1x | 100 | 127 | 113.5 | 113.5 | 44.1% | 0.073 |
| BC2 (AAX3) | 58 | 1x | 29 | 29 | 29 | 29 | 50.0% | 1.000 |

TABLE 2-continued

| Generation (line) | No | Gly. S.R. | Obs. Tol. | Obs. Sens. | Exp. Tol. | Exp. Sens. | % Tol. | CHI test value |
|---|---|---|---|---|---|---|---|---|
| BC3 (AAX3) | 74 | 1x | 38 | 36 | 37 | 37 | 51.4% | 0.816 |

Abbreviations:
Gen.: Generation;
No: Number of plants;
Gly. S.R.: glyphosate spray rate;
Obs. Tol: observed tolerant;
Obs. Sens.: observed sensitive;
Exp. Tol.: expected tolerant;
Obs. Tol: expected sensitive;
% Tol.: % Tolerant.

All plants were evaluated two weeks after spraying. A segregation ratio of 1:1 was expected in each generation because epsps grg23ace5 is present at single and hemizygous copy in the donor parental line crossed with the lines B109, B110 or AAX3.

Observed segregation patterns were compared to the expected patterns and these data were compared using a chi-squared ($X^2$) distribution analysis, as follows:

$X^2 = \Sigma[(|o-e|)^2/e]$, where o=observed frequency of tolerance, and e=expected frequency of tolerance.

A chi-square value of ≥0.05 was treated as the cutoff for statistical support of a 1:1 segregation in each generation, and this value was exceeded for each of the segregation analysis groups. The results of this analysis are consistent with the inheritance of a single copy of epsps grg23ace5 into each of the inbred lines tested (B110, B109, AAX3).

Transformation event VCO-Ø1981-5 contains a single genetic insertion of the epsps grg23ace5 gene, and that gene is inherited through successive breeding generations in the predictable Mendelian fashion.

VI. Method of Detection of the VCO-Ø1981-5 Event:

This example describes an event-specific real-time quantitative TaqMan PCR method for determination of the relative content of event VCO-Ø1981-5 DNA to total maize (Zea mays) DNA in a biological sample.

The PCR assay has been optimized for use in an ABI Prism® 7900 sequence detection system.

For specific detection of event VCO-Ø1981-5 genomic DNA, a 85-bp fragment of the region that spans the 5' TDNA insert and flanking genomic junction in maize event VCO-Ø1981-5, is amplified using two specific primers. PCR products are measured during each cycle (real-time) by means of a target-specific oligonucleotide probe labelled with a fluorescent dye: FAM as a reporter dye at its 5' end and MGBmolecule as a quencher at its 3' end. The 5'-nuclease activity of the Taq DNA polymerase is exploited, which results in the specific cleavage of the probe, leading to increased fluorescence, which is then monitored. For relative quantification of event VCO-Ø1981-5 DNA, a maize specific reference system amplifies a 70-bp fragment of aldolase (Kelley et al., 1986), a maize endogenous sequence, using a pair of aldolase gene-specific primers and an aldolase gene-specific probe labelled with VIC and TAMRA.

Two types of quantification are simultaneously performed in this method: one for the endogenous gene aldolase and one for the event VCO-Ø1981-DNA region. The following sets of primers and probes are used.

TABLE 3

| | Sequence (5' to 3') |
|---|---|
| VCO-Ø1981-5 primer F | Ccactgaacgtcaccaagaaga (SEQ ID NO: 11) |
| VCO-Ø1981-5 primer R | Gccgctactcgagggattta (SEQ ID NO: 12) |
| VCO-Ø1981-5 probe | 6-FAM-cagtactcaaacactgatag-MGB (SEQ ID NO: 13) |
| Aldolase primer F | Agggaggacgcctccct (SEQ ID NO: 14) |
| Aldolase primer R | Accctgtaccagaagaccaagg (SEQ ID NO: 15) |
| Aldolase probe | 6-VIC-tgaggacatcaacaaaagg cttgcca-TAMRA (SEQ ID NO: 16) |

The master-mix for the aldolase reference gene system is prepared as followed in Table 4:

TABLE 4

| Component | Final concentration in PCR | µl/reaction |
|---|---|---|
| TaqMan ® Universal Master Mix 2X | 1x | 12.5 |
| Primer F (5 µM) | 300 nM | 1.5 |
| Primer R (5 µM) | 300 nM | 1.5 |
| Probe (5 µM) | 200 nM | 1.0 |
| Nuclease free water | # | 6.0 |
| Template DNA (maximum 200 ng) | # | 2.5 |
| Total volume: | | 25 µl |

The master-mix for VCO-Ø1981-5 event is prepared as followed in Table 5:

TABLE 5

| Component | Final concentration in PCR | µl/reaction |
|---|---|---|
| TaqMan ® Universal Master Mix 2X | 1x | 12.5 |
| Primer F (5 µM) | 300 nM | 1.5 |
| Primer R (5 µM) | 300 nM | 1.5 |
| Probe (5 µM) | 200 nM | 1.0 |
| Nuclease free water | # | 6.0 |
| Template DNA (maximum 200 ng) | # | 2.5 |
| Total volume: | | 25 µl |

Run the PCR with cycling conditions listed below for both VCO-Ø1981-5 event and aldolase assays in the Applied Biosystems 7900 system.

TABLE 6

| Step | Stage | | T ° C. | Time (sec) | Data collection | Cycles |
|---|---|---|---|---|---|---|
| 1 | Uracil-DNA-N Glycosylase (UNG) | | 50° C. | 120" | no | 1x |
| 2 | Initial denaturation | | 95° C. | 600" | no | 1x |
| 3 | Amplification | Denaturation | 95° C. | 15" | no | 40x |
| | | Annealing & Extension | 60° C. | 60" | yes | |

VII. Evaluation of Agronomic Performance of Event VCO-Ø1981-5

In order to evaluate agronomic performance characteristics of event VCO-Ø1981-5 as compared to an appropriate negative isoline, two experimental varieties were produced and seed used for multiple location evaluation. The experimental varieties are hybrid maize obtained by crossing the event VCO-Ø1981-5 (BC2S2) with two different lines (B116 and CH01). Negative segregants crossed with the lines B116 and CH01 were used as comparators (see table 5 and FIG. 3 for breeding diagram).

TABLE 7

Maize hybrids tested in agronomic evaluations.

| Line Tested | Pedigree |
|---|---|
| VCO-Ø1981-5 (A) | BC0S2 VCO-Ø1981-5 × B116 |
| Control: Negative isoline (A) | BC0S2 null × B116 |
| VCO-Ø1981-5 (B) | BC0S2 VCO-Ø1981-5 × CH01 |
| Control: Negative isoline (B) | BC0S2 null × CH01 |

These hybrids were characterized under diverse environmental and growing conditions similar to those used in maize production. The study was conducted using a Randomized Complete Block design with three replications (plots) of each entry per location. Each plot consisted of four, 30-inch rows by 17.5 to 20 ft. long. Plants were thinned prior to reaching the V8 leaf stage resulting in a uniform number of plants in each row. Weeds outside of the plots (in alleyways and borders) managed as to not confound measures of agronomic characteristics. Weeds within the plots were managed by conventional herbicides and cultural practices (hand hoeing). No broad spectrum herbicides were applied to the study or borders rows except as a pre-plant or pre-emergence application. Data on all traits was collected on the middle two rows of each four row plot. Data collected over season is summarized in Tables 8 and 9.

TABLE 8

Agronomic performance results-vegetative characteristics

| Agronomic Characteristic (unit) | Genetic Background | VCO-Ø1981-5 Corn | Number of plants | Control | Number of plants | |
|---|---|---|---|---|---|---|
| Plant height (inches) | B116 | 116.9 | 49 | 113.5 | 44 | Mean |
| | | 32.0-136.5 | 36-72 | 26.7-138.5 | 27-72 | Range |
| | | 0.7918 | 0.0067 | | 0.0067 | p-value |
| | CH01 | 110.4 | 48 | 106.8 | 46 | Mean |
| | | 32.7-124.8 | 36-72 | 21.7-130.7 | 31-72 | Range |
| | | 0.7632 | 0.01797 | | 0.01797 | p-value |
| Grain weight (pounds per plot) | B116 | 19.5 | 49 | 18.2 | 44 | Mean |
| | | 3.8-27.0 | 36-72 | 4.0-37.4 | 27-72 | Range |
| | | 0.2292 | 0.0067 | | 0.0067 | p-value |
| | CH01 | 19.9 | 48 | 18.8 | 46 | Mean |
| | | 6.0-30.6 | 36-72 | 2.0-31.1 | 31-72 | Range |
| | | 0.3662 | 0.01797 | | 0.01797 | p-value |

TABLE 9

Agronomic performance results - reproductive parameters

| Agronomic Characteristic (unit) | Genetic Background (same as in Table 8) | VCO-Ø1981-5 Corn | Control | |
|---|---|---|---|---|
| Days to 50% pollen shed (# days) | B116 | 72.6 | 73.3 | Mean |
| | | 59-95 | 59-94 | Range |
| | | 0.6978 | | p-value |
| | CH01 | 72.3 | 72.9 | Mean |
| | | 57-93 | 56-94 | Range |
| | | 0.7365 | | p-value |
| Days to 50% silking (# days) | B116 | 74.6 | 75.0 | Mean |
| | | 59-97 | 59-95 | Range |
| | | 0.8087 | | p-value |
| | CH01 | 72.6 | 72.8 | Mean |
| | | 57-96 | 56-96 | Range |
| | | 0.9003 | | p-value |
| Yield (bushel per acre) | B116 | 143.0 | 130.7 | Mean |
| | | 35.6-218.9 | 26.5-228.7 | Range |
| | | 0.1584 | | p-value |
| | CH01 | 150.4 | 138.6 | Mean |
| | | 52.4-259.7 | 18.3-222.1 | Range |
| | | 0.1896 | | p-value |

REFERENCES

Basra A., 1999. Heterosis and Hybrid Seed Production in Agronomic Crops (The Harwoth Press Inc.).

Bernardo R., 2010. Breeding for quantitative traits in plants (2$^{nd}$ ed, Stemma press.com).

Cheng, Z. M., Schnurr, J. A. and Kapaun, J. A., 1998. Timentin as an alternative antibiotic for suppression of Agrobacterium tumefaciens in genetic transformation. Plant Cell Reports. 646-649.

De la Riva, G. A., Gonzalez-Cabrera, J., Vazquez-Padron, R., and Ayra-Pardo, C., 1998. Agrobacterium tumefaciens: A Natural Tool for Plant Transformation. Elec. J. of Biotech., 1, 118-133.

Dellaporta S. L., Wood, J. and. Hicks, J. B., 1983. A plant DNA minipreparation: version II Plant Molecular Biology Reporter, 1, 19-21.

Depicker, A., Stachel, S., Dhaese, P., Zambryski, P., and Goodman, H. M. J., 1982. Molecular Applied Genetics, 1, 561-574.

EFSA journal "Guidance for risk assessment of food and feed genetically modified plant, 2011; 9(5): 2150, p 10).

Fang, L., Gross, P., Chen, C. and Lillis, M., 1992. Sequence of two acetohydroxyacid synthase genes from Zea mays, Plant Molecular Biology, 18, 1185-1187.

Freeling M. and Walbot V., 1994. The Maize Handbook, Springer Lab Manuals.

Gardner, R., Howarth, A., Hahn, P., Brown-Luedi, M., Shepherd, R., and Messing, J., 1981. The complete nucleotide sequence of an infectious clone of cauliflower mosaic virus by M13mp7 shotgun sequencing, Nucleic Acids Research, 9, 2871-2888.

Gelvin, S. B. 2005. Agricultural biotechnology: Gene exchange by Design. Nature 433, 583-584.

Hallauer A. and Miranda J. B., 1988. Quantitative genetics in maize breeding. 2nd edition, Iowa State University press.

Kelley P. M. and Tolan D. R., 1986. The complete amino acid sequence for the anaerobically induced aldolase from maize derived from cDNA clones. Plant Physiol. 82, 1076-1080.

Komari, T., Hiei, Y., Saito, Y., Mural, N., and Kumashiro, T. 1996. Vectors carrying two separate T-DNAs for co-transformation of higher plants mediated by Agrobacterium tumefaciens and segregation of transformants free from selection markers. Plant J 10:165-174.

Lawrence C. J., Dong Q., Polacco M. L., Seigfried T. E., Brendel V., 2004. Maize GDB, the community database for maize genetics and genomics. Nucleic Acids Res. 32. Database issue D393-D397.

Otten, L., Salomone, J. Y., Helfer, A., Schmidt, J., Hammann, P. and De Ruffray, P. 1999 Sequence and functional analysis of the left-hand part of the T-region from the nopaline-type Ti plasmid, pTiC58 Plant Mol. Biol. 41 (6), 765-776.

Pena L., 2005. Transgenic Plants: Methods and Protocols. Methods in Molecular Biology, Vol 286 Humana Press Inc.

Sambrook, J., Fritsch, E. F., and Maniatis T., 1989. Molecular Cloning, A Laboratory Manual. Second edition. Cold Spring Harbor Laboratory Press.

The invention claimed is:

1. A glyphosate tolerant maize plant comprising in its genome the nucleotide sequence as set forth in SEQ ID NO: 3.

2. The glyphosate tolerant maize plant of claim 1, wherein the glyphosate tolerant maize plant is obtained by breeding a maize plant with a maize plant grown from seeds deposited with NCIMB with accession number 41842.

3. The glyphosate tolerant maize plant of claim 2, wherein the glyphosate tolerant maize plant is an hybrid maize plant.

4. The glyphosate tolerant maize plant of claim 1, wherein a part of the glyphosate tolerant maize plant, cells or seeds comprise a nucleotide sequence as set forth in SEQ ID NO: 3.

* * * * *

SEQUENCE LISTING

<160> NUMBER OF SEQ ID NOS: 23

<210> SEQ ID NO 1
<211> LENGTH: 24
<212> TYPE: DNA
<213> ORGANISM: artificial
<220> FEATURE:
<223> OTHER INFORMATION: minimal sequence junction in 5'

<400> SEQUENCE: 1
ccaagaagat cagtactcaa acac                                          24

<210> SEQ ID NO 2
<211> LENGTH: 25
<212> TYPE: DNA
<213> ORGANISM: artificial
<220> FEATURE:
<223> OTHER INFORMATION: minimal sequence junction in 3'

<400> SEQUENCE: 2
tttacaccgt tctcagaggg agatg                                         25

<210> SEQ ID NO 3
<211> LENGTH: 5092
<212> TYPE: DNA
<213> ORGANISM: artificial
<220> FEATURE:
<223> OTHER INFORMATION: total sequence of the T-DNA insert and the
      flanking genomic sequence

<400> SEQUENCE: 3
tttcctcatt ttcttttcc cgcttttgtt tcaattttc ttgggtaatg tacagtgagt      60
atattttttc ttgttctttt tctcatggcc aaaatccaca atggatcgat gaattagctg    120
tcgttgttgc caacaacaac aacagaacaa aatcacgtga cgtactagca caatgcaagt    180
agccaaactg agcttccggg caccgacgaa cggttgcacg ccatcggcgg aaggaacag     240 gccgggctgt caatggacaa acgggccgcc aagctggagg gagtgtcatg ggctttgaga    300
accatcgtca gggtccagtt tattcttttg tttttattaa aggcggtaaa ctcggggaac    360
gaatatacta ggaaaaacac tagccagtca gagtcagtca aagtggactg agttaaaatt    420
gcaacgacac acacgcagca gtcagggcgt cgggaatgaa caatggatga atttattata    480
atctgaagaa aacgaaggga cacagccact acgaacactg gggagtgggg agtgaatgaa    540
tgaatgcatt ccactggacc gttccagcgc ttcgtgtgcc tcgctagatg cgctgaacac    600
tcgaacgcca tggacctcgc tccgctctct atatatagag ggaaggcctt cagtctactc    660
ctcgggatat accactgaac gtcaccaaga agatcagtac tcaaacactg atagtttaaa    720
ctgaagaagc ttaatttaaa tccctcgagt agcggccgct agcccgggca tagcttaatt    780
cattatgtgg tctaggtagg ttctatatat aagaaaactt gaaatgttct aaaaaaaaat    840
tcaagcccat gcatgattga agcaaacggt atagcaacgg tgttaacctg atctagtgat    900
ctcttgcaat ccttaacggc cacctaccgc aggtagcaaa cggcgtcccc ctcctcgata    960
tctccgcggc gacctctggc ttttccgcg gaattgcgcg gtggggacgg attccacgag    1020
accgcgacgc aaccgcctct cgccgctggg ccccacaccg ctcggtgccg tagcctcacg    1080
ggactctttc tccctcctcc cccgttataa attggcttca tccctcctt gcctcatcca    1140 tccaaatccc agtccccaat cccatcccctt cgtcggagaa attcatcgaa gcgaagcgaa    1200
tcctcgcgat cctctcaagg tactgcgagt tttcgatccc cctctcgacc cctcgtatgt    1260

```
ttgtgtttgt cgtagcgttt gattaggtat gctttccctg tttgtgttcg tcgtagcgtt      1320
tgattaggta tgctttccct gttcgtgttc atcgtagtgt ttgattaggt cgtgtgaggc      1380
gatggcctgc tcgcgtcctt cgatctgtag tcgatttgcg ggtcgtggtg tagatctgcg      1440
ggctgtgatg aagttatttg gtgtgatctg ctcgcctgat tctgcgggtt ggctcgagta      1500
gatatgatgg ttggaccggt tggttcgttt accgcgctag ggttgggctg ggatgatgtt      1560
gcatgcgccg ttgcgcgtga tcccgcagca ggacttgcgt ttgattgcca gatctcgtta      1620
cgattatgtg atttggtttg gacttttag atctgtagct tctgcttatg tgccagatgc      1680
gcctactgct catatgcctg atgataatca taaatggctg tggaactaac tagttgattg      1740
cggagtcatg tatcagctac aggtgtaggg actagctaca ggtgtaggga cttgcgtcta      1800
attgtttggt cctttactca tgttgcaatt atgcaattta gtttagattg tttgttccac      1860
tcatctaggc tgtaaaaggg acactgctta gattgctgtt taatcttttt agtagattat      1920
attatattgg taacttatta ccctattac atgccatacg tgacttctgc tcatgcctga      1980
tgataatcat agatcactgt ggaattaatt agttgattgt tgaatcatgt ttcatgtaca      2040
taccacggca caattgctta gttccttaac aaatgcaaat tttactgatc catgtatgat      2100
ttgcgtggtt ctctaatgtg aaatactata gctacttgtt agtaagaatc aggttcgtat      2160
gcttaatgct gtatgtgcct tctgctcatg cctgatgata atcatatatc actggaatta      2220
attagttgat cgtttaatca tatatcaagt acataccatg gcacaatttt tagtcactta      2280
acccatgcag attgaactgg tccctgcatg ttttgctaaa ttgttctatt ctgattagac      2340
catatatcat gtattttttt ttggtaatgg ttctcttatt ttaaatgcta tatagttctg      2400
gtacttgtta gaaagatctg cttcatagtt tagttgccta tccctcgaat taggatgctg      2460
agcagctgat cctatagctt tgtttcatgt atcaattctt ttgtgttcaa cagtcagttt      2520
ttgttagatt cattgtaact tatggtcgct tactcttctg gtcctcaatg cttgcagctg      2580
cagaccatgg ccaccgccgc cgccgcgtct accgcgctca ctggcgccac taccgctgcg      2640
cccaaggcga ggcgccgggc gcacctcctg gccacccgcc gcgccctcgc cgcgcccatc      2700
aggtgctcag cggcgtcacc cgccatgccg atggctcccc cggccacccc gctccggccg      2760
tggggcccca ccgatccccg caagggatcc ggcatggaaa ctgatcgcct tgtgatccca      2820
ggatcgaaaa gcatcaccaa ccgggctttg cttttggctg ccgcagcgaa gggcacgtcg      2880
gtcctggtga gaccattggt cagcgccgat acctcagcat tcaaaactgc aatccaggcc      2940
ctcggtgcca acgtctcagc cgacggtgac gattgggtcg ttgaaggcct gggtcaggca      3000
cccaacctcg acgccgacat ctggtgcgag gacgcaggta ctgtggcccg gttcctccct      3060
ccattcgtag ccgcaggtca ggggaagttc accgtcgacg gatcagagca gctgcggcgg      3120
cgcccgcttc ggcccgtggt cgacggcatc cgccacctgg gcgcccgcgt ctcctccgag      3180
cagctgcccc ttacaattga agcgagcggg ctggcaggcg gggagtacga aattgaagcc      3240
catcagagca gccagttcgc ctccggcctg atcatggccg ccccgtacgc gagacaaggc      3300
ctgcgtgtga agataccaaa tcccgtgtca cagccctacc tcacgatgac actgcggatg      3360
atgagggact tcggcattga gaccagcacc gacggagcca ccgtcagcgt ccctccaggg      3420
cgctacacag cccggcggta tgaaatagaa ccggatgcgt caactgcgtc gtacttcgcc      3480
gccgcttccg ccgtctctgg caggcgcttc gaatttcaag gccttggcac agacagcatc      3540
caaggcgaca cgtcattctt caatgtactt gggcggctcg gtgcggaggt ccactgggca      3600
tccaactcgg tcaccatacg gggaccggaa aggctgaccg gcgacattga agtggatatg      3660
```

```
ggcgagattt cggacacctt catgacactc gcggcgattg cccctttggc cgatggaccc     3720
atcacgataa ccaacattgg tcatgcacgg ttgaaggaat ccgaccgcat ctcagcgatg     3780
gaaagcaacc tgcgcacgct cggtgtacaa accgacgtcg acacgactg gatgagaatc      3840 taccccctcta ccccgcacgg cggtagagtg aattgccacc gggaccacag gatcgctatg    3900
gcgttttcaa tcctgggact gagagtggac gggattaccc tcgacgaccc tcaatgcgtc     3960
gggaagacct ttcctggctt cttcgactac cttggacgcc ttttcccga aaaggcgctt      4020 acgctccccg gctagggcgc gcctccttcg aagaccctt cctctatata aggaagttca      4080
tttcatttgg agaggacacg ctgaaatcac cagtctctct ctacaaatct atctctctct     4140
attttctcca taataatgtg tgagtagttc ccagataagg gaattagggt tcttataggg     4200
tttcgctcac gtgttgagca tataagaaac cctagtatg tatttgtatt tgtaaaatac      4260
ttctatcaat aaaatttcta attcctaaaa ccaaaatcca gtactaaaat ccactcgaga     4320
cgcgtgaatt cagtacatta aaaacgtccg caatgtgtta ttaagttgtc taagcgtcaa     4380
tttgtttaca ccgttctcag agggagatgg gcggcaaggg cggcgggggt ggtggcaagg     4440
gcggcggcgg gggtggtggc aagggcggag gaggttttgg tggcaagagc ggcggcgggg    4500
gtggtggcaa gggcggagga ggtgttggtg gcaagagcgg cggcggcaag tcaggcggcg    4560
gcggcggtgg gggctatggt ggtggaggga agtcaggctc cggcggcagt ggcggcgacg    4620
gaatgatgaa ggcgcccggc ggcagtggcg agtacatctc ccgctctgtc ttcgaggcca    4680
gcccgcaggt gttcttccat ggcctccacc agggaggagg caacaacaag tagatccatc    4740
tagctagact gctgctgcta cttcacaagc ttgggacgat gtgtgatcat gcatgcttgg    4800
actggcatca gtctctatgt agcttctgaa taaaataaaa tgtaacgatg ctcgattgtg    4860
tttcacttgc tcgcttgttt cagccaagtt attatatatc atcaggctcg tacgtcagct    4920
atatatatat atatatatat atatatatat atatatatat atatatatat atatatatat    4980
atatatatat atatatatat atatatacac acacacacat atgcaggtgc atggattgtg    5040
caacgcgaat gtgtgattgt gctaatccgt tagttgatgc cgtttgttgc tt             5092
```

<210> SEQ ID NO 4
<211> LENGTH: 364
<212> TYPE: DNA
<213> ORGANISM: Saccharum officinarum

<400> SEQUENCE: 4

```
aattcattat gtggtctagg taggttctat atataagaaa acttgaaatg ttctaaaaaa       60
aaattcaagc ccatgcatga ttgaagcaaa cggtatagca acggtgttaa cctgatctag      120
tgatctcttg caatccttaa cggccaccta ccgcaggtag caaacggcgt cccctcctc       180 gatatctccg cggcgaccte tggcttttc cgcggaattg cgcggtgggg acggattcca      240
cgagaccgcg acgcaaccgc ctctcgccgc tgggccccac accgctcggt gccgtagcct     300
cacgggactc tttctccctc ctcccccgtt ataaattggc ttcatcccct ccttgcctca     360
tcca                                                                   364
```

<210> SEQ ID NO 5
<211> LENGTH: 1358
<212> TYPE: DNA
<213> ORGANISM: Saccharum officinarum

<400> SEQUENCE: 5

| | |
|---|---|
| gtactgcgag ttttcgatcc ccctctcgac ccctcgtatg tttgtgtttg tcgtagcgtt | 60 |
| tgattaggta tgcttttccct gtttgtgttc gtcgtagcgt ttgattaggt atgctttccc | 120 |
| tgttcgtgtt catcgtagtg tttgattagg tcgtgtgagg cgatggcctg ctcgcgtcct | 180 |
| tcgatctgta gtcgatttgc gggtcgtggt gtagatctgc gggctgtgat gaagttattt | 240 |
| ggtgtgatct gctcgcctga ttctgcgggt tggctcgagt agatatgatg gttggaccgg | 300 |
| ttggttcgtt taccgcgcta gggttgggct gggatgatgt tgcatgcgcc gttgcgcgtg | 360 |
| atcccgcagc aggacttgcg tttgattgcc agatctcgtt acgattatgt gatttggttt | 420 |
| ggactttta gatctgtagc ttctgcttat gtgccagatg cgcctactgc tcatatgcct | 480 |
| gatgataatc ataaatggct gtggaactaa ctagttgatt gcggagtcat gtatcagcta | 540 |
| caggtgtagg gactagctac aggtgtaggg acttgcgtct aattgtttgg tcctttactc | 600 |
| atgttgcaat tatgcaattt agtttagatt gtttgttcca ctcatctagg ctgtaaaagg | 660 |
| gacactgctt agattgctgt ttaatctttt tagtagatta tattatattg gtaacttatt | 720 |
| accctatta catgccatac gtgacttctg ctcatgcctg atgataatca tagatcactg | 780 |
| tggaattaat tagttgattg ttgaatcatg tttcatgtac ataccacggc acaattgctt | 840 |
| agttccttaa caaatgcaaa ttttactgat ccatgtatga tttgcgtggt tctctaatgt | 900 |
| gaaatactat agctacttgt tagtaagaat caggttcgta tgcttaatgc tgtatgtgcc | 960 |
| ttctgctcat gcctgatgat aatcatatat cactggaatt aattagttga tcgtttaatc | 1020 |
| atatatcaag tacataccat ggcacaattt ttagtcactt aacccatgca gattgaactg | 1080 |
| gtccctgcat gttttgctaa attgttctat tctgattaga ccatatatca tgtatttttt | 1140 |
| tttggtaatg gttctcttat tttaaatgct atatagttct ggtacttgtt agaaagatct | 1200 |
| gcttcatagt ttagttgcct atccctcgaa ttaggatgct gagcagctga tcctatagct | 1260 |
| ttgtttcatg tatcaattct tttgtgttca acagtcagtt tttgttagat tcattgtaac | 1320 |
| ttatggtcgc ttactcttct ggtcctcaat gcttgcag | 1358 |

<210> SEQ ID NO 6
<211> LENGTH: 198
<212> TYPE: DNA
<213> ORGANISM: Zea mays

<400> SEQUENCE: 6

| | |
|---|---|
| atggccaccg ccgccgccgc gtctaccgcg ctcactggcg ccactaccgc tgcgcccaag | 60 |
| gcgaggcgcc gggcgcacct cctggccacc cgccgcgccc tcgccgcgcc catcaggtgc | 120 |
| tcagcggcgt cacccgccat gccgatggct ccccggcca ccccgctccg gccgtggggc | 180 |
| cccaccgatc cccgcaag | 198 |

<210> SEQ ID NO 7
<211> LENGTH: 1242
<212> TYPE: DNA
<213> ORGANISM: Arthrobacter globiformis

<400> SEQUENCE: 7

| | |
|---|---|
| atggaaactg atcgccttgt gatcccagga tcgaaaagca tcaccaaccg ggctttgctt | 60 |
| ttggctgccg cagcgaaggg cacgtcggtc ctggtgagac cattggtcag cgccgatacc | 120 |
| tcagcattca aaactgcaat ccaggccctc ggtgccaacg tctcagccga cggtgacgat | 180 |
| tgggtcgttg aaggcctggg tcaggcaccc aacctcgacg ccgacatctg gtgcgaggac | 240 |
| gcaggtactg tggcccggtt cctccctcca ttcgtagccg caggtcaggg gaagttcacc | 300 |

```
gtcgacggat cagagcagct gcggcggcgc ccgcttcggc ccgtggtcga cggcatccgc    360
cacctgggcg cccgcgtctc ctccgagcag ctgccccta caattgaagc gagcgggctg     420
gcaggcgggg agtacgaaat tgaagcccat cagagcagcc agttcgcctc cggcctgatc    480
atggccgccc cgtacgcgag acaaggcctg cgtgtgaaga taccaaatcc cgtgtcacag    540
ccctacctca cgatgacact gcggatgatg agggacttcg gcattgagac cagcaccgac    600
ggagccaccg tcagcgtccc tccagggcgc tacacagccc ggcggtatga aatagaaccg    660
gatgcgtcaa ctgcgtcgta cttcgccgcc gcttccgccg tctctggcag gcgcttcgaa    720
tttcaaggcc ttggcacaga cagcatccaa ggcgacacgt cattcttcaa tgtacttggg    780
cggctcggtg cggaggtcca ctgggcatcc aactcggtca ccatacgggg accggaaagg    840
ctgaccggcg acattgaagt ggatatgggc gagatttcgg acaccttcat gacactcgcg    900
gcgattgccc ctttggccga tggacccatc acgataacca acattggtca tgcacggttg    960
aaggaatccg accgcatctc agcgatgaaa agcaacctgc gcacgctcgg tgtacaaacc   1020
gacgtcggac acgactggat gagaatctac ccctctaccc cgcacggcgg tagagtgaat   1080
tgccaccggg accacaggat cgctatgcg ttttcaatcc tgggactgag agtggacggg    1140
attaccctcg acgaccctca atgcgtcggg aagaccttc ctggcttctt cgactacctt    1200
ggacgccttt tccccgaaaa ggcgcttacg ctccccggct ag                      1242

<210> SEQ ID NO 8
<211> LENGTH: 270
<212> TYPE: DNA
<213> ORGANISM: Cauliflower mosaic virus

<400> SEQUENCE: 8
tccttcgcaa gacccttcct ctatataagg aagttcattt catttggaga ggacacgctg     60
aaatcaccag tctctctcta caaatctatc tctctctatt ttctccataa taatgtgtga    120
gtagttccca gataagggaa ttagggttct atagggtttc gctcacgtg ttgagcatat     180 aagaaaccct agtatgtat ttgtatttgt aaaatacttc tatcaataaa atttctaatt    240
cctaaaacca aaatccagta ctaaaatcca                                     270

<210> SEQ ID NO 9
<211> LENGTH: 700
<212> TYPE: DNA
<213> ORGANISM: artificial
<220> FEATURE:
<223> OTHER INFORMATION: flanking 5' genomic sequence

<400> SEQUENCE: 9
gttctcagag ggagatgggc ggcaagggcg gcggggtgg tggcaagggc ggcggcgggg      60
gtggtggcaa gggcggagga ggttttggtg gcaagagcgg cggcggggt ggtggcaagg    120 gcggaggagg tgttggtggc aagagcggcg gcggcaagtc aggcggcggc ggcggtgggg    180
gctatggtgg tggagggaag tcaggctccg gcggcagtgg cggcgacgga atgatgaagg    240
cgcccggcgg cagtggcgag tacatctccc gctctgtctt cgaggccagc ccgcaggtgt    300
tcttccatgg cctccaccag ggaggaggca acaacaagta gatccatcta gctagactgc    360
tgctgctact tcacaagctt gggacgatgt gtgatcatgc atgcttggac tggcatcagt    420
ctctatgtag cttctgaata aaataaaatg taacgatgct cgattgtgtt tcacttgctc    480
gcttgtttca gccaagttat tatatatcat caggctcgta cgtcagctat atatatat    540
```

```
atatatatat atatatatat atatatatat atatatatat atatatatat atatatatat     600
atatatatat atatacacac acacacatat gcaggtgcat ggattgtgca acgcgaatgt     660
gtgattgtgc taatccgtta gttgatgccg tttgttgctt                          700
```

<210> SEQ ID NO 10
<211> LENGTH: 700
<212> TYPE: DNA
<213> ORGANISM: artificial
<220> FEATURE:
<223> OTHER INFORMATION: flanking 5' genomic sequence

<400> SEQUENCE: 10

```
atttcgagcg atttaagtat gcacagtata tagccttcat atgcatttta ataatttctg      60
tcaattatct actacgggaa ataaaagtag aaaaataaag tccagaacta atgcatgaac     120
atagcacatc aggtgtaaca agaattttac catattcaag catgtatttt tgcactaatt     180
atttgcgaca ggaaataatt aatgaagata taaattgcga tagaaaaaca tgcttagttt     240
tatttattat ttgcatcatt aatcatgaaa tatcatagaa ttaataatag ggagcatgat     300
tataaattta tataaattca gcaggaattt tatttatata aaaaaacaag aataagatta     360
gcaacttagt cgaattaaat caaaaaatgc taaggaggcg ccattatcct atgtgcataa     420
gcacgctatg gatcccatga ccgtagcctt ttctgttgac cgcacatgca atatgaccat     480
tgcatgcatg cacctcatgc actttgactt tgactggatc ttttcttacg ttggttggat     540
gaggtcgctg cttatccgtg gcatgcagtg ccgcattcga agcgagcgga gggagagatt     600
cggttttcgc tctctttccc gtatatcctt atcttcacga ctggttcaca tgcgtggccg     660
gctctggcgt tccacaccag gcatcttggc gtaggactcc                          700
```

<210> SEQ ID NO 11
<211> LENGTH: 22
<212> TYPE: DNA
<213> ORGANISM: artificial
<220> FEATURE:
<223> OTHER INFORMATION: VCO-01981-5 primer F

<400> SEQUENCE: 11

```
ccactgaacg tcaccaagaa ga                                              22
```

<210> SEQ ID NO 12
<211> LENGTH: 20
<212> TYPE: DNA
<213> ORGANISM: artificial
<220> FEATURE:
<223> OTHER INFORMATION: VCO-01981-5 primer R

<400> SEQUENCE: 12

```
gccgctactc gagggattta                                                 20
```

<210> SEQ ID NO 13
<211> LENGTH: 20
<212> TYPE: DNA
<213> ORGANISM: artificial
<220> FEATURE:
<223> OTHER INFORMATION: VCO-01981-5 probe

<400> SEQUENCE: 13

```
cagtactcaa acactgatag                                                 20
```

<210> SEQ ID NO 14
<211> LENGTH: 17

```
<212> TYPE: DNA
<213> ORGANISM: artificial
<220> FEATURE:
<223> OTHER INFORMATION: Aldolase primer F

<400> SEQUENCE: 14
agggaggacg cctccct                                                      17

<210> SEQ ID NO 15
<211> LENGTH: 22
<212> TYPE: DNA
<213> ORGANISM: artificial
<220> FEATURE:
<223> OTHER INFORMATION: Aldolase primer R

<400> SEQUENCE: 15
accctgtacc agaagaccaa gg                                                22

<210> SEQ ID NO 16
<211> LENGTH: 26
<212> TYPE: DNA
<213> ORGANISM: artificial
<220> FEATURE:
<223> OTHER INFORMATION: Aldolase probe

<400> SEQUENCE: 16
tgaggacatc aacaaaaggc ttgcca                                            26

<210> SEQ ID NO 17
<211> LENGTH: 27
<212> TYPE: DNA
<213> ORGANISM: artificial
<220> FEATURE:
<223> OTHER INFORMATION: primer Ace5-1

<400> SEQUENCE: 17
acaggatcgc tatggcgttt tcaatcc                                           27

<210> SEQ ID NO 18
<211> LENGTH: 28
<212> TYPE: DNA
<213> ORGANISM: artificial
<220> FEATURE:
<223> OTHER INFORMATION: primer Ace5-2

<400> SEQUENCE: 18
atgcgtcggg aagacctttc ctggcttc                                          28

<210> SEQ ID NO 19
<211> LENGTH: 27
<212> TYPE: DNA
<213> ORGANISM: artificial
<220> FEATURE:
<223> OTHER INFORMATION: primer O39

<400> SEQUENCE: 19
caccagggag gaggcaacaa caagtag                                           27

<210> SEQ ID NO 20
<211> LENGTH: 27
<212> TYPE: DNA
<213> ORGANISM: artificial
<220> FEATURE:
<223> OTHER INFORMATION: primer Scubi-NewR

<400> SEQUENCE: 20
```

```
agaaagagtc ccgtgaggct acggcac                                            27
```

<210> SEQ ID NO 21
<211> LENGTH: 28
<212> TYPE: DNA
<213> ORGANISM: artificial
<220> FEATURE:
<223> OTHER INFORMATION: primer Scubi2-Rev

<400> SEQUENCE: 21

```
ctgggatttg gatggatgag gcaaggag                                           28
```

<210> SEQ ID NO 22
<211> LENGTH: 27
<212> TYPE: DNA
<213> ORGANISM: artificial
<220> FEATURE:
<223> OTHER INFORMATION: Scubi1-Rev

<400> SEQUENCE: 22

```
agaggtcgcc gcggagatat cgaggag                                            27
```

<210> SEQ ID NO 23
<211> LENGTH: 413
<212> TYPE: PRT
<213> ORGANISM: artificial
<220> FEATURE:
<223> OTHER INFORMATION: protein sequence GRG23ACE5

<400> SEQUENCE: 23

```
Met Glu Thr Asp Arg Leu Val Ile Pro Gly Ser Lys Ser Ile Thr Asn
1               5                   10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Lys Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
```

```
                        225                 230                 235                 240

Phe Gln Gly Leu Gly Thr Asp Ser Ile Gln Gly Asp Thr Ser Phe Phe
                        245                 250                 255

Asn Val Leu Gly Arg Leu Gly Ala Glu Val His Trp Ala Ser Asn Ser
                        260                 265                 270

Val Thr Ile Arg Gly Pro Glu Arg Leu Thr Gly Asp Ile Glu Val Asp
                    275                 280                 285

Met Gly Glu Ile Ser Asp Thr Phe Met Thr Leu Ala Ala Ile Ala Pro
                290                 295                 300

Leu Ala Asp Gly Pro Ile Thr Ile Thr Asn Ile Gly His Ala Arg Leu
        305                 310                 315                 320

Lys Glu Ser Asp Arg Ile Ser Ala Met Glu Ser Asn Leu Arg Thr Leu
                        325                 330                 335

Gly Val Gln Thr Asp Val Gly His Asp Trp Met Arg Ile Tyr Pro Ser
                        340                 345                 350

Thr Pro His Gly Gly Arg Val Asn Cys His Arg Asp His Arg Ile Ala
                    355                 360                 365

Met Ala Phe Ser Ile Leu Gly Leu Arg Val Asp Gly Ile Thr Leu Asp
                370                 375                 380

Asp Pro Gln Cys Val Gly Lys Thr Phe Pro Gly Phe Phe Asp Tyr Leu
        385                 390                 395                 400

Gly Arg Leu Phe Pro Glu Lys Ala Leu Thr Leu Pro Gly
                        405                 410
```